(12) United States Patent
Hares (10) Patent No.: US 10,639,110 B2
(45) Date of Patent: May 5, 2020

(54) COOLING A SURGICAL ROBOTIC ARM

(71) Applicant: CMR SURGICAL LIMITED, Cambridge (GB)

(72) Inventor: Luke David Ronald Hares, Milton (GB)

(73) Assignee: CMR Surgical Limited, Cambridge (GB)

( * ) Notice: Subject to any disclaimer, the term of this patent is extended or adjusted under 35 U.S.C. 154(b) by 296 days.

(21) Appl. No.: 15/527,561

(22) PCT Filed: Nov. 19, 2015

(86) PCT No.: PCT/GB2015/053540
§ 371 (c)(1),
(2) Date: May 17, 2017

(87) PCT Pub. No.: WO2016/079532
PCT Pub. Date: May 26, 2016

(65) Prior Publication Data
US 2017/0360516 A1    Dec. 21, 2017

(30) Foreign Application Priority Data

Nov. 20, 2014   (GB) .................................. 1420607.2

(51) Int. Cl.
  *A61B 34/30*  (2016.01)
  *A61B 46/10*  (2016.01)
  *F24F 13/02*  (2006.01)
  *A61B 18/00*  (2006.01)
(52) U.S. Cl.
  CPC .............. *A61B 34/30* (2016.02); *A61B 46/10* (2016.02); *A61B 2018/00023* (2013.01); *F24F 13/0218* (2013.01)

(58) Field of Classification Search
  CPC ................... A61B 34/30; A61B 46/10; A61B 2018/00023; F24F 13/0218
  See application file for complete search history.

(56) References Cited

U.S. PATENT DOCUMENTS

| 5,122,904 A | 6/1992 | Fujiwara et al. |
| 5,345,480 A | 9/1994 | de Magny |
| 5,970,980 A | 10/1999 | Adair |
| 8,202,278 B2 | 6/2012 | Orban, III et al. |

(Continued)

FOREIGN PATENT DOCUMENTS

| EP | 0138461 | 4/1985 |
| EP | 0664101 | 7/1995 |

(Continued)

OTHER PUBLICATIONS

Search Report regarding priority application GB1420607.2, dated Apr. 25, 2015 (5pgs.).

(Continued)

*Primary Examiner* — Yan Lan
(74) *Attorney, Agent, or Firm* — Renner, Otto, Boisselle & Sklar, LLP (57) ABSTRACT

A surgical robotic arm drape for enveloping a portion of a robotic arm, the drape comprising: an exterior sheet defining an elongate cavity for housing a portion of a robotic arm; and a duct defined at least in part by material integral with the exterior sheet, the duct defining a fluid path along the longitudinal extent of the cavity to channel fluid to or from a robotic arm housed within the cavity.

8 Claims, 9 Drawing Sheets

(56) References Cited

U.S. PATENT DOCUMENTS

2005/0143625 A1 6/2005 Whitmore, III et al.
2005/0161176 A1 7/2005 Brenner et al.

FOREIGN PATENT DOCUMENTS

EP 2700374 2/2014
WO 2013160239 10/2013

OTHER PUBLICATIONS

International Search Report regarding PCT/GB2015/053540, dated Jun. 4, 2016 (6pgs.).
Written Opinion of the International Searching Authority regarding PCT/GB2015/053540, dated Jun. 4, 2016 (9pgs.).

COOLING A SURGICAL ROBOTIC ARM

FIELD

This invention relates to providing cooling to a surgical robotic arm.

BACKGROUND

Figure 1:
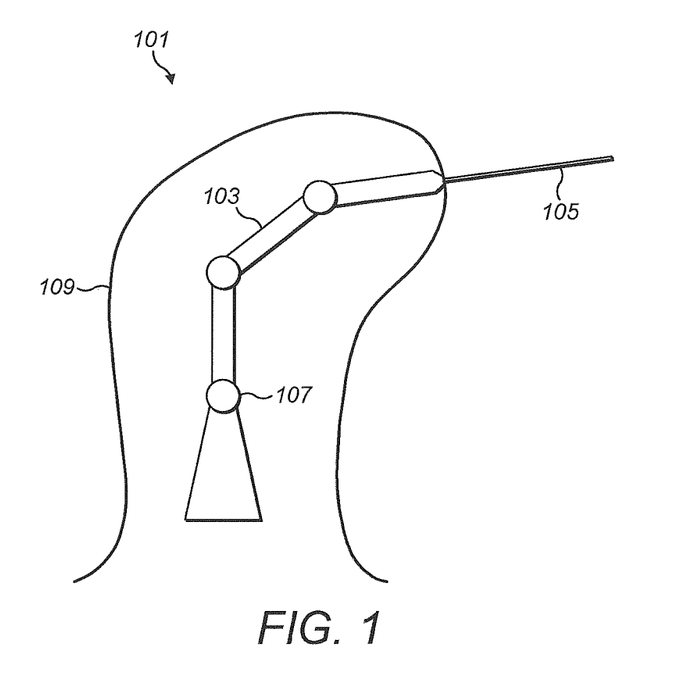
FIG. 1 shows a conventional surgical robot and drape.

FIG. 1 shows a typical surgical robot for performing robotic surgery. The surgical robot 101 comprises a robotic arm 103 attached at one of its ends to a surgical instrument 105. The surgical instrument is operable to pass into a patient for performing surgery. The robotic arm comprises one or more joints 107 about which the arm can be articulated to control the movement and/or position of the surgical instrument. FIG. 1 also shows a surgical robotic drape 109 which shrouds the robotic arm to provide a sterile boundary between the surgical instrument (which must be sterile) and the robotic arm (which is not necessarily sterile).

The robotic drape is an effective low-cost solution for maintaining a sterile surgical environment which negates the need for sterilising the robotic arm. The surgical instrument (which is typically of substantially lower cost than the robotic arm) can be made to be disposable after each use to ensure adequate surgical hygienic standards are maintained, or can be sterilized (e.g. in an autoclave) after use. However, a problem with the drape is that by enclosing the robotic arm it may cause the arm (in particular the motors driving articulation about the joints) to overheat. This problem may be exacerbated by the fact that the motors used within robotic arms are often designed to be relatively small so as to reduce the weight and size of the arm, which means that during operation the motors are operating at a relatively high rotation speed and therefore generate large amounts of heat.

One approach to provide cooling is to integrate ducts within the robotic arm that channel cooling fluid, for example cool air or possibly a liquid coolant, into and out of the robotic arm. However, it is often advantageous and desirable for robotic arms to be made to minimise bulk and weight. For example, one advantage of a smaller, more lightweight robotic arm from the viewpoint of a surgeon is that it may improve the usability and manoeuvrability of the surgical robot; from the point of view of the patient, a smaller robotic arm may appear less intrusive, or intimidating. Consequently, space within the robotic arm is often at a premium, meaning it may be impractical or difficult to install ducts that both channel fluid to the arm and ducts that channel fluid away from the arm.

There is therefore a need for an improved way of cooling a surgical robotic arm.

SUMMARY

According to the present invention there is provided a surgical robotic arm drape for enveloping a portion of a robotic arm, the drape comprising: an exterior sheet defining an elongate cavity for housing a portion of a robotic arm; and a duct defined at least in part by material integral with the exterior sheet, the duct defining a fluid path along the longitudinal extent of the cavity to channel fluid to or from a robotic arm housed within the cavity.

The duct may be defined substantially wholly by material of the exterior sheet.

The duct may be attached to the exterior sheet and is defined substantially wholly by material integral with the exterior sheet.

The duct may comprise a first opening configured so as to be positioned in the vicinity of a robotic arm housed within the cavity, and a second opening configured so as to be in the vicinity of an opening in the cavity, wherein the first opening extends away from the exterior sheet towards the interior of the cavity for connecting to a robotic arm housed within the cavity.

The duct may be sufficiently rigid so as to maintain an open fluid path when there exists a negative pressure in the duct relative to the exterior of the drape during use caused by the second opening being under suction.

The duct may be tubular.

The duct may comprise silicone.

The duct may be defined in part by material integral with the exterior sheet and in part by the exterior sheet.

The said material may be in a nested arrangement with the exterior sheet along the longitudinal extent of the cavity.

The said material may be in a concentric arrangement with the exterior sheet along the longitudinal extent of the cavity.

The duct may comprise a first opening configured so as to be positioned in the vicinity of a robotic arm housed within the cavity, and a second opening configured so as to be in the vicinity of an opening in the cavity, and wherein the drape comprises spacing elements positioned within the duct so as to maintain an open fluid path when there exists a negative pressure in the duct relative to the exterior of the drape during use caused by the second opening being under suction.

The spacing elements may comprise a plurality of projections extending at least partly between the said material and the exterior sheet.

The projections may be in the form of ribs.

The duct may be defined by a plurality of ribs integral with the exterior sheet.

The ribs may be configured so as to connect to an exterior surface of a robotic arm housed within the cavity during use.

The duct may extend along the longitudinal extent of the cavity in a linear arrangement.

The duct may extend along the longitudinal extent of the cavity in a helical arrangement.

The duct may comprise first and second terminal openings and at least one port situated between the first and second terminal openings, the at least one port arranged to channel fluid to and from a respective at least one location on a robotic arm housed within the cavity.

According to a second aspect of the present invention there is provided a surgical robotic arm, the robotic arm comprising surface features extending along a longitudinal extent thereof, wherein the surface features are configured to cooperate with a surgical robotic arm drape enveloping a portion of the robotic arm to define a duct for channelling fluid to or from the robotic arm.

The surface features may comprise a channel extending along a longitudinal extent of the robotic arm.

The surface features may comprise a plurality of ribs projecting substantially radially outward from the robotic arm for engaging a surgical robotic arm drape when the drape envelopes a portion of the robotic arm.

The robotic arm may further comprise a grating covering the channel for engaging a surgical robotic arm drape when the drape envelopes a portion of the robotic arm.

According to a third aspect of the present invention there is provide a surgical robotic apparatus, comprising: a surgical robotic arm; and a surgical robotic arm drape for enveloping a portion of the robotic arm, the drape comprising an exterior sheet defining an elongate cavity for housing a portion of the robotic arm; and longitudinal features operable to space the exterior sheet of the drape from an outer surface of the robotic arm when there is a negative pressure within the cavity relative to an adjacent region exterior of the cavity to define a fluid path to channel fluid to or from the robotic arm housed within the cavity.

BRIEF SUMMARY OF THE DRAWINGS

The present invention will now be described by way of example with reference to the accompanying drawings. In the drawings.

FIG. $2_A$ shows a surgical robotic arm drape in use with a surgical robot.

FIG. $2_B$ shows a surgical robotic arm drape in use with a surgical robot.

FIG. $3_A$ shows a surgical robotic arm drape comprising a duct that is formed substantially wholly by material integral with the sheet of the drape.

FIG. $3_B$ shows a cross-sectional view of the surgical robotic arm drape shown in FIG. $3_A$.

FIG. $7_A$ shows a partial cut-away of a surgical robotic arm drape comprising a duct defined in part by material integral with the exterior sheet of the drape, and in part by the exterior sheet.

FIG. $7_B$ is a plan cross-sectional view of the surgical drape shown in FIG. $7_A$.

DETAILED DESCRIPTION

Embodiments of the present invention are directed to using the surgical robotic drape to help provide cooling to a robotic arm.

Embodiments of the present invention use the surgical robotic drape to assist in providing cooling to the robotic arm. The drape comprises a flexible sheet. In certain embodiments the drape may define one or both of (a) an inward fluid path for leading cooling fluid to the robotic arm and (b) a return fluid path for leading cooling fluid from the robotic arm. The fluid may be a liquid or a gas. If the drape provides paths of both types there may be no need for an integrated duct within the robotic arm. Alternatively the drape may provide a fluid path that runs either from or to the robotic arm but not both. In this case the robotic arm itself may comprise an integrated duct to provide the opposite path: for example, fluid may be channelled through the integrated duct of the robotic arm and away from the robotic arm through the fluid path defined by the drape, or alternatively fluid may be channelled to the robotic arm through the fluid path defined by the drape and away from the robotic arm through the integrated duct.

The drape may be used to provide cooling to the robotic arm in a number of ways. In a first set of arrangements the drape may comprise a duct that defines the fluid path for channelling fluid to and/or from a robotic arm that is enveloped by the drape. The duct may be in the form of an enclosed tube that runs along the wall of the drape. In an alternative set of arrangements the duct may be defined by the robotic arm and the drape in combination: for example the duct may comprise interior surface features that partially define a duct and the robotic arm may comprise exterior surface features that cooperate with the interior surface features of the drape to define an enclosed duct when the drape is installed in place on the arm. In each case, the duct can be for channelling fluid to and/or from the robotic arm.

Use of the drape to provide a fluid path to channel fluid to and/or from the robotic arm is a particularly convenient solution for providing cooling to the robotic arm. Because surgical drapes are often designed to be low-cost and readily replaceable, using the drape to provide the cooling can provide a low-cost way to help reduce the risk of overheating robotic arms. It may also enable cooling to be provided whilst minimising the required number of ducts integral with the arm, thereby allowing a more efficient design of robotic arm to be realised.

Figure 2A:
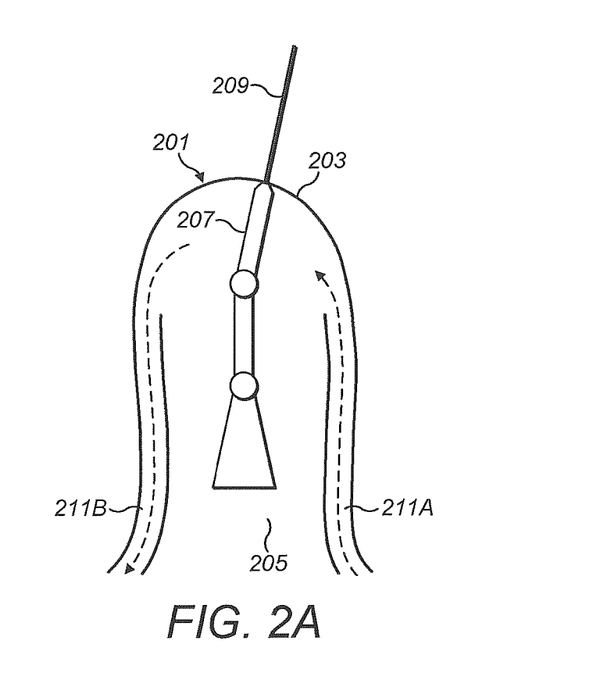

FIG. $2_A$ is a schematic diagram of a surgical robotic drape according to an embodiment of the present invention. As shown, the drape 201 comprises an exterior sheet 203 which defines an elongate cavity 205. Housed within the cavity is a robotic arm 207. The surgical instrument 209 used for performing surgery passes through a distal end of the drape and extends on the sterile side of the barrier defined by the drape. The drape comprises an opening, or mouth, at its proximal end that permits the drape to be passed over the arm. The mouth may be sealed against the arm to enclose a volume between the interior of the drape and the exterior of the arm. The drape comprises ducts $211_A$ and $211_B$ which define a fluid path along the longitudinal extent of the cavity. That is, the ducts extend along the general longitudinal direction of the cavity so as to enable fluid to be channelled to and from the robotic arm housed within the cavity. Duct $211_A$ defines a fluid path to channel fluid to the robotic arm and duct $211_B$ defines a fluid path to channel fluid away from the robotic arm. An exemplary flow path is illustrated by the dashed arrow.

The general path of the fluid is therefore into the cavity via duct $211_A$, around the robotic arm housed within the cavity and then out of the cavity through duct $211_B$. The fluid flow through the cavity acts to cool the robotic arm housed therein. The fluid flow may be driven by blowing fluid into the cavity via duct $211_A$; by drawing fluid out via duct $211_B$ (for example by placing the outlet of the duct under suction), or a combination of these features.

The fluid may be a gas, for example air or carbon dioxide. The fluid may be a liquid, for example water, ethylene glycol or liquid nitrogen. The liquid or gas may be cooled to a temperature below room temperature before being fed to the robotic arm so as increase the cooling effect on the robotic arm.

The embodiment shown in FIG. $2_A$ comprises ducts that define a fluid path into the cavity to the robotic arm and out of the cavity away from the robotic arm. The embodiment may therefore advantageously negate the need for the robotic arm to have an integral fluid duct.

Figure 2B:
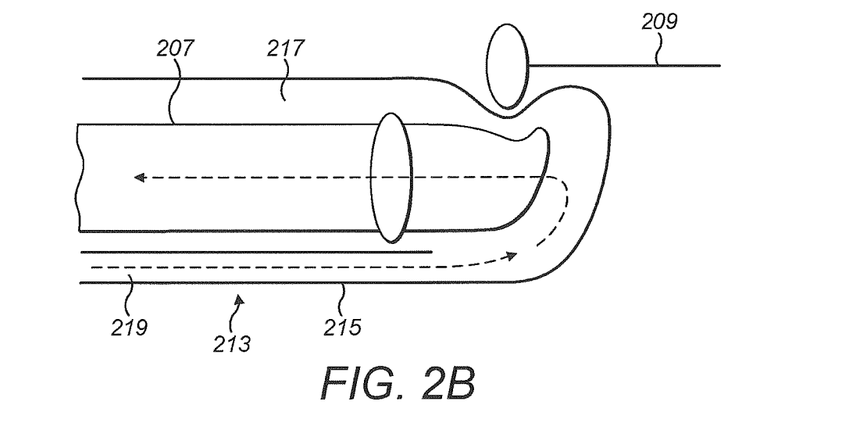

FIG. $2_B$ shows an alternative embodiment of a surgical robotic drape. Drape 213 comprises an exterior sheet 215 defining an elongate cavity 217 for housing a portion of robotic arm 207. Attached to the distal end of arm 207 is a surgical instrument 209, which as shown is on the sterile side of the boundary defined by the exterior sheet. In this embodiment the drape comprises a duct 219 that defines a fluid path along the longitudinal extent of the cavity to channel fluid to the robotic arm. Fluid channelled to the robotic arm through duct 219 is channelled out of the cavity through a duct within the robotic arm (not shown). The fluid path through the arm is denoted by the dashed arrow.

Alternatively the duct 219 may be used to channel fluid from the robotic arm. In this arrangement fluid may be channelled into the duct internal to the arm 207. Fluid output from that duct is then channelled away from the arm and out of the cavity through duct 219. In either arrangement it can be seen that the duct 219 contributes to providing a path for fluid to flow into and out of the cavity so as to provide a cooling effect to a robotic arm housed therein.

The fluid flow through the duct may be driven by a component external to the drape. For example, fluid may be driven through the duct towards the robotic arm using a pump, or fan. Alternatively fluid may be drawn out of the duct and channelled away from the robotic arm by placing an opening of the duct under suction. For example an opening of the duct may be connected to a component external to the drape that places the connected opening under suction. The opening placed under suction may be near the mouth the drape. Actively driving fluid through the duct may assist in increasing the rate of fluid flow towards or away from the robotic arm, thereby increasing the potential cooling effect. To further increase the rate of fluid flow, fluid may be driven through the duct of the arm 207 in conjunction with the driving of fluid through the duct of the drape. For example if fluid is being driven through duct 219 to the distal end of the robotic arm (as shown), the proximal end of the arm may be placed under suction so as to draw fluid through the robotic arm and out of the cavity. Or, vice versa, if fluid is being drawn out of the duct 219 to channel fluid from the distal end of the robotic arm, fluid may also be driven up through the duct at the proximal end of the robotic arm.

In either of the embodiments shown in FIGS. $2_A$ and $2_B$, the ducts may extend out of the elongate cavity so as to channel fluid between a point exterior of the cavity and a point interior of the cavity. Alternatively the duct may be positioned entirely within the cavity and fluid channelled into and out of the cavity via an additional adapter, or connector, for example a connector that connects the duct of the drape to a pump or fan external of the drape.

The drape ducts illustrated generally in FIGS. $2_A$ and $2_B$ may be formed in various ways according to different embodiments of the present invention. Various examples of how the duct may be formed are described below.

Figure 3A:
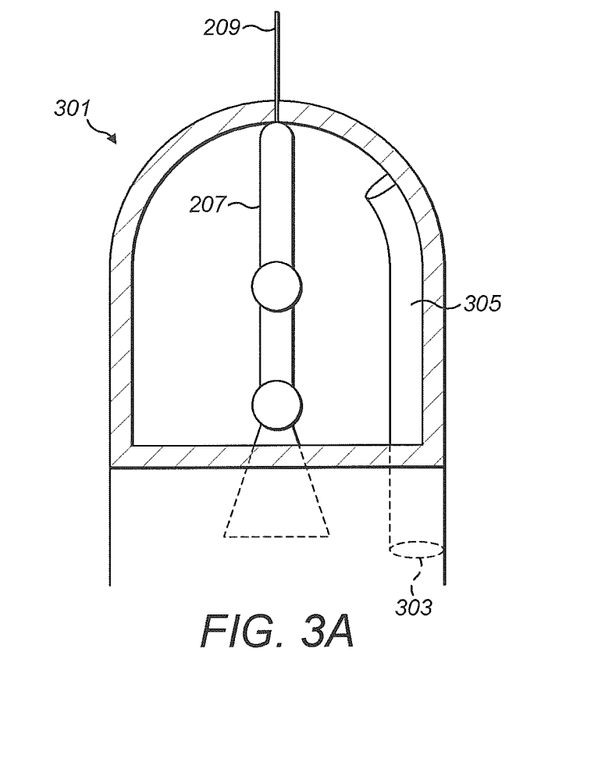

The drape duct may be defined at least in part by material that is integral with the exterior sheet. The duct could be defined by the material of the exterior sheet; or additional material can be made integral with the exterior sheet of the drape so as to form the duct. In one set of embodiments, the duct may be defined substantially wholly by the additional material integral with the sheet. For example, the material may be formed into a tubular duct that is then attached to the exterior sheet. A schematic diagram of such an embodiment is shown in FIG. 3.

Figure 3B:
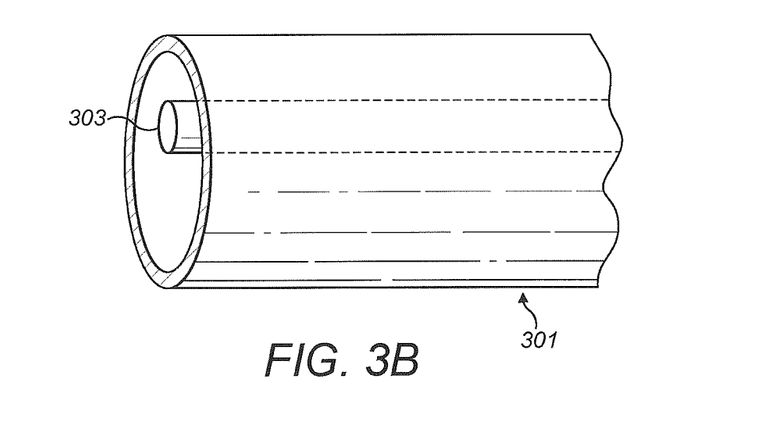

Shown in FIG. $3_A$ is a surgical robotic arm drape 301 with an exterior sheet defining an elongate cavity as described previously. The drape is shown with a portion cut-away for the purposes of illustration. The drape 301 comprises a duct 303 formed from an additional material 305 and secured to the exterior sheet. The duct may be secured to the exterior sheet of the drape in a number of ways, for example using an adhesive. A cross-sectional view of the drape is shown in FIG. $3_B$, where the robotic arm has been omitted for clarity. Here it can be seen that the duct 303 is secured to the exterior sheet so as to be within the cavity housing the robotic arm 207.

It has been described that to cool the robotic arm an outlet of the drape duct may be placed under suction to drive the flow of fluid away from the robotic arm, through the duct and out of the cavity. This outlet may be near the mouth of the drape. Operating the drape in this way may cause a 'shrink-wrap' effect in which the exterior sheet of the drape is drawn in towards the outer surface of the robotic arm due to the negative pressure within the cavity relative to the exterior of the cavity caused by the suction of fluid through the duct. To prevent this pressure difference from collapsing the duct and blocking the flow of fluid therethrough, the duct may suitably be made sufficiently rigid so as to maintain an open fluid path even when such a negative pressure exists. The duct may be made by sufficiently rigid by suitable choice of the material 305 and its thickness. The material and its thickness may be chosen in dependence on the expected pressure difference between the cavity and exterior of the drape during use. The required thickness of the material will depend on the type of material chosen and vice versa. The material may be silicone.

Figure 4:
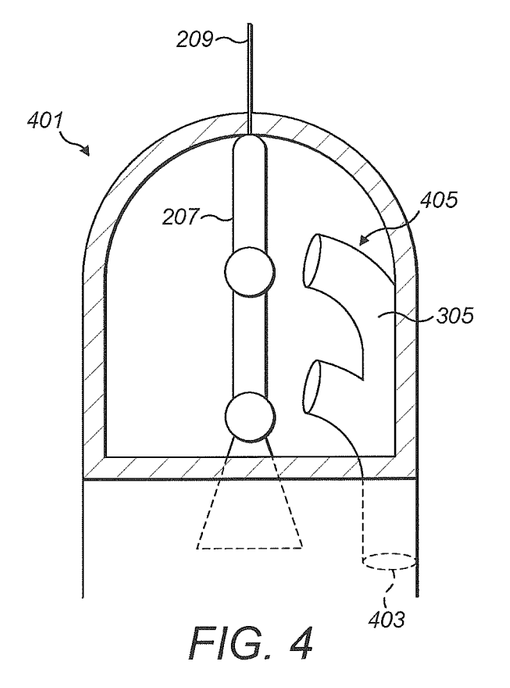
FIG. 4 shows a surgical robotic arm drape comprising a duct that extends towards a robotic arm housed within a cavity defined by the drape.

In the embodiment shown in FIG. 3 the duct extends along the longitudinal extent of the cavity so that an opening of the duct 303 is in the general vicinity of an opening of the duct for the robotic arm 207. However it may be desirable for the opening of the drape duct to join or connect to a part of the robotic arm housed within the cavity in order to improve the channelling of fluid to or from the robotic arm (and therefore increase the cooling effect). An example of a drape comprising such a duct is shown in FIG. 4.

The drape 401 comprises duct 403 which is formed from material 305 and which is attached along part of its length to the exterior sheet of the cavity. The exterior of the drape is partially cut away for the purposes of clarity. A portion of the duct 405 extends away from the exterior sheet towards the interior region of the cavity for connecting to a section of the robotic arm housed therein. The duct may be configured to extend away from the exterior sheet so as to connect or attach to a section of the robotic arm that has particularly high cooling demands. This may be in the region of a joint, as shown, due to the proximity of motors used to actuate the arm. The opening of the duct may be securable to the robotic arm by attachments, for example using hooks or clips. Alternatively the duct may be attached to the arm using a non-permanent adhesive, such as a weak glue.

The material 305 may be chosen so as to permit a degree of flexibility and compliance in the duct. This may aid a user in manoeuvring the portion 405 to a position in which the opening is secured to a desired section of the robotic arm. The material could be, for example, silicone, or some other type of synthetic rubber compound.

Manufacturing the duct substantially wholly out of an additional material 305 and then securing the formed duct to the exterior sheet provides a convenient, low-cost approach to using the surgical drape to assist in the cooling of a robotic arm. For example it may advantageously allow for the modification of existing low-cost surgical drapes. In addition, tubular-like ducts, for example ducts 303 and 403, can be manufactured relatively easily and cheaply from material 305, meaning that the surgical robotic arm drape can advantageously be used to provide cooling to a housed robotic arm whilst still remaining a relatively low-cost, disposable item.

In the example embodiments described above with reference to FIGS. 3 and 4, the duct was formed substantially wholly by the material integral with the exterior sheet of the drape. In alternative embodiments the duct may be defined in part by the material integral with the exterior sheet, and in part by the exterior sheet itself. For example a sheet or panel of material may be attached to the exterior sheet so as to define the duct in the region between the material and the exterior sheet. An example of a drape comprising a duct formed in this manner is shown in FIG. 5.

Figure 5:
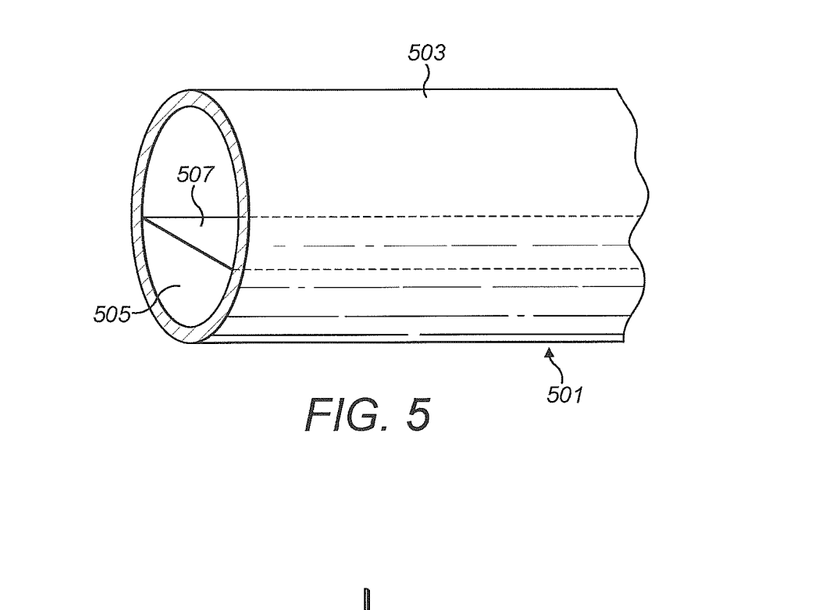
FIG. 5 is a cross-sectional view of a surgical robotic arm drape comprising a duct defined in part by material integral with the exterior sheet of the drape and in part by the exterior sheet.

FIG. 5 shows a cross-sectional cutaway of a drape 501, where the housed robotic arm has been omitted for the purposes of clarity. As before the drape comprises an exterior sheet 503 which defines the elongate cavity, and a duct 505 defined in part by material 507 integral with the exterior sheet, and in part by the exterior sheet itself. As before the duct defines a fluid path along the longitudinal extent of the cavity to channel fluid to or from the robotic arm. In this case the fluid flows in the region bounded on one side by the exterior sheet and on the other side by the material 507.

Figure 6:
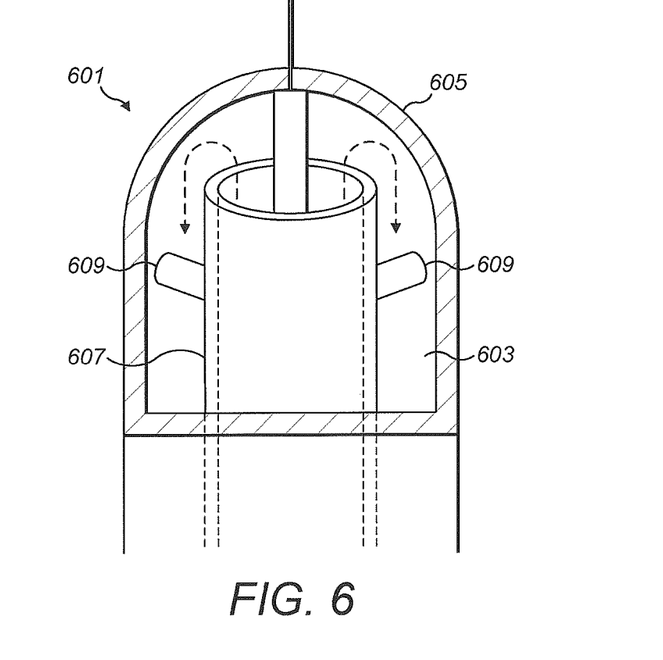
FIG. 6 shows a partial cut-away of a surgical robotic arm drape comprising a duct defined in part by material integral with the exterior sheet of the drape and in part by the exterior sheet.

In an alternative arrangement, the exterior sheet and the material defining the duct in conjunction with the exterior sheet may be in a nested arrangement when viewed in a cross-section perpendicular to the longitudinal extent of the cavity. This arrangement is shown in FIG. 6, where the drape is shown with a portion of the exterior sheet cut away for the purpose of clarity. Here the surgical drape 601 comprises a duct 603 defined in part by the exterior sheet 605 of the drape and in part by material 607 that is integral with the sheet. Because the material 607 is nested within the exterior sheet along the longitudinal extent of the cavity, fluid may be channelled to and from multiple sides of the robotic arm 207 housed within the cavity. That is, the opening of the duct 603 may encircle the robotic arm (as shown) to enable fluid to be channelled to and from more sides of the robotic arm as compared to the embodiments shown in FIGS. 2 to 5, which may enhance the cooling effect provided by the drape.

Material 607 may be nested within the exterior sheet in a concentric arrangement. In this arrangement the duct has an annular cross-sectional profile when viewed along the longitudinal extent of the cavity.

The material 607 may be made integral with the exterior sheet by one or more connections 609 which can function to support and hold the material relative to the sheet. The connections may be made of the same material as material 607 or a different material.

When the drape duct is defined in part by the material integral with the exterior sheet and in part by the exterior sheet itself, the drape may further comprise spacing elements positioned within the duct so as to prevent the duct from collapsing and blocking the fluid path when there is a negative pressure in the duct relative to the exterior of the drape. As discussed above, this negative pressure may arise when outlets of the duct are placed under suction so as channel air away from the robotic arm and out of the cavity in the direction of the dashed arrow indicated in FIG. 6.

The spacing elements may be in the form of projections extending at least partly between the exterior sheet and material integral with the exterior sheet. The projections may be attached to the material and/or the exterior sheet. The projections may be in the form of mounds so as not to substantially impede the fluid flow through the duct. The mounds may project in a direction substantially perpendicular to the longitudinal extent of the cavity. The mounds may be in cylindrical or conical form.

In one embodiment the projections may be in the form of one or more ribs attached to the material 507,607 and/or the exterior sheet. If the ribs are attached to the material and the sheet there may be no need for the connectors 609 as the function of securing the material relative to the exterior sheet will be performed by the ribs. The ribs may extend along the longitudinal extent of the cavity. The ribs may extend along the same length as the duct, though they may alternatively extend along a shorter length. The number of ribs may depend on the size of the drape duct. For example, the duct 505 of FIG. 5 may only require one rib whereas the annular duct 605 may require more than one rib.

Figure 7A:
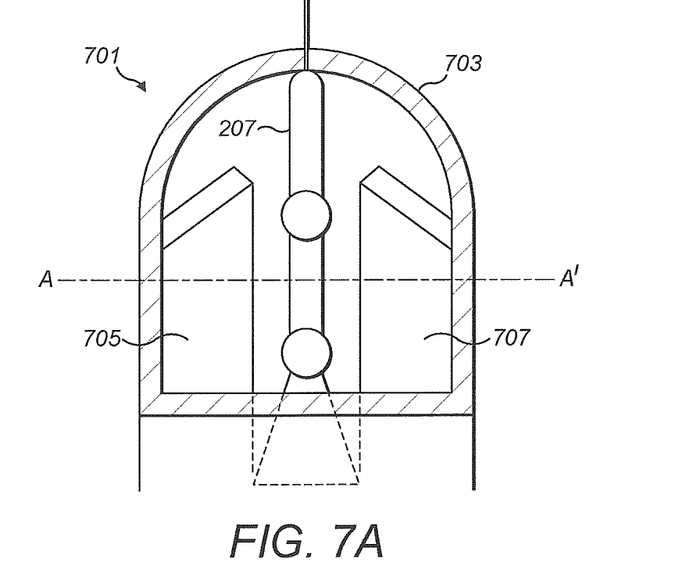
Figure 7B:
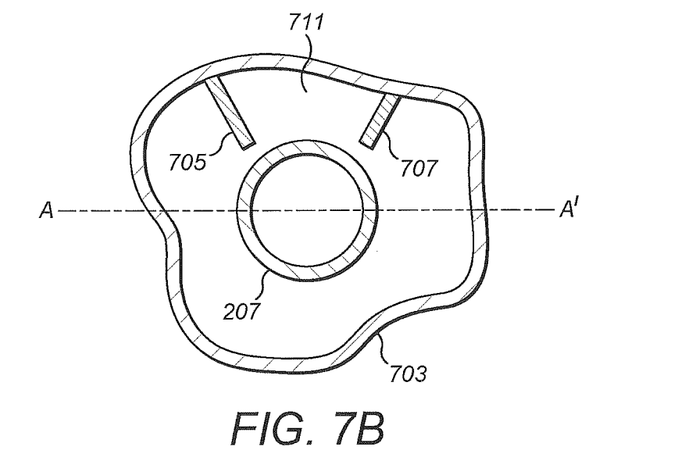

In another alternative embodiment the material integral with the exterior sheet that in part defines the duct may be in the form of a plurality of ribs. A surgical drape according to this embodiment is shown in FIG. 7. The drape 701 comprises an exterior sheet 703 defining an elongate cavity as previously described. A portion of the exterior of the drape is shown cut away for the purposes of clarity. The drape comprises a plurality of ribs 705 and 707 each integral with the exterior sheet 703 and positioned approximately circumferentially when viewed in cross-section perpendicularly to axis A-A', as shown at 709 in FIG. $7_B$. In this embodiment the duct 711 is defined in part by the two ribs and the portion of the exterior sheet therebetween. In use the duct defines a fluid path to channel fluid to or from the robotic arm housed within the cavity, with fluid flowing in the region bounded by the two ribs and the portion of exterior sheet therebetween. This embodiment may have the advantage that the fluid flows across the surface of the robotic arm for the duration of the length of the duct as opposed to being separated from the surface of the robotic arm by the boundary of the duct, as in previous embodiments. This may lead to a greater cooling of a robotic arm housed within the drape.

It will be appreciated that the effectiveness of the duct 711 at channelling fluid to and from the robotic arm will be increased when the ribs are in contact with, or drawn in towards, the outer surface of the robotic arm. For this reason the arrangement shown in FIG. 7 may be particularly suitable for use when the outlet of the duct is under suction to channel fluid from the robotic arm and out of the drape. When this happens the negative pressure within the duct relative to the exterior of the drape will cause the ribs to be drawn towards the arm in a similar manner to the shrink-wrap effect described above. This arrangement has the further advantage that the drape does not require any further spacing elements since the function of spacing the exterior sheet from the robotic arm is performed by the ribs 705, 707.

Although only two ribs are shown in FIG. 7, it will be appreciated that in other embodiments there may be more than two ribs so as to define more than one duct.

In the embodiments described so far the drape duct has generally been depicted as having two terminal openings: a first terminal opening located generally towards the opening of the cavity and a second terminal opening located within the cavity within the general vicinity of a section of the robotic arm. However for each of these embodiments the duct may further comprise at least one port situated between the terminal openings for channelling fluid to and from a respective at least one location on the robotic arm. A schematic diagram of a surgical drape with a duct comprising such a port is shown in FIG. 8.

Figure 8:
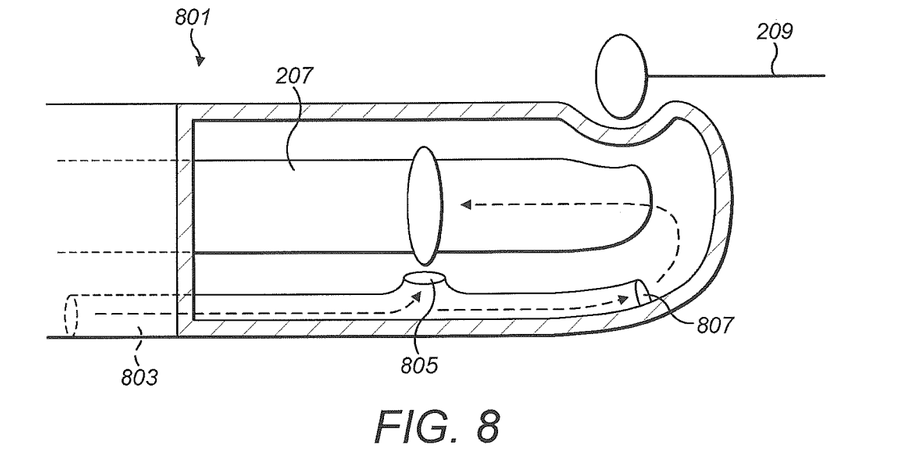
FIG. 8 shows a partial cut-away of a surgical robotic arm drape in use with a surgical robot, the drape comprising a duct with a side port.

As shown in FIG. 8 the surgical drape 801 comprises a duct 803 which has a port 805 situated between the terminal openings (of which only one is shown, depicted at 807). The port 805 functions to channel fluid to or from a location on the robotic arm in addition to the terminal opening 807. This may be particularly useful if the robotic arm has more than one region which would benefit from receiving fluid flow. For example if the arm comprises more than one joint it may be advantageous to channel fluid to or from each joint in order to improve cooling of the motors housed in the arm in proximity to the joints. Although only one port 805 is shown in FIG. 8, it will be appreciated that there could be any suitable number of ports situated between the terminal openings of the duct.

Thus far various embodiments have been described in which a surgical drape comprises a duct for channelling fluid to or from a robotic arm. In some embodiments the duct is defined substantially wholly by material integral with the exterior sheet; in other embodiments the duct is defined in part by the material integral with the exterior sheet and in part by the exterior sheet. It will be appreciated that for each of these embodiments the duct may be configured so as to extend along the longitudinal extent of the drape cavity in various arrangements.

In one arrangement, the duct may extend along the longitudinal extent of the cavity in a linear arrangement, for example as shown generally in FIGS. 2 to 8. This provides a relatively simple and low-cost construction. In an alternative arrangement, the duct may be provided in a helical arrangement, as illustrated in FIG. 9.

Figure 9:
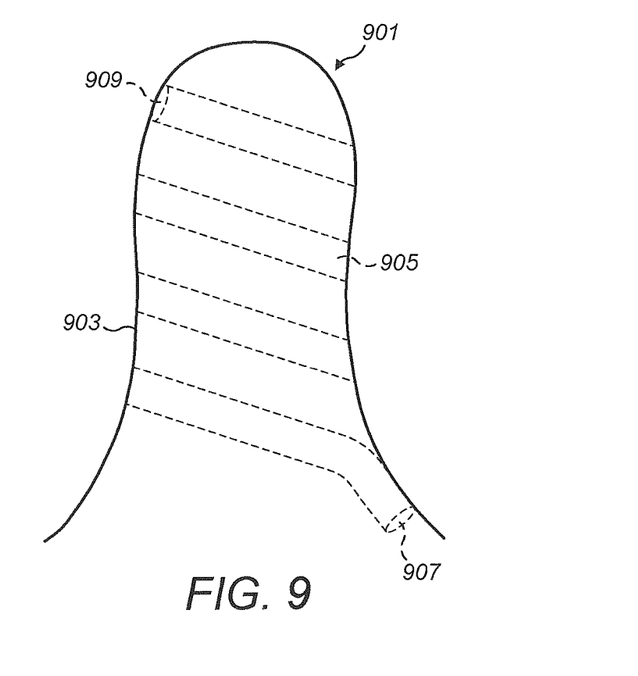
FIG. 9 shows a surgical robotic arm drape comprising a duct in a helical arrangement.

As shown in FIG. 9 a surgical drape 901 comprises an exterior sheet 903 defining an elongate cavity. The robotic arm to be housed within the cavity has been omitted for clarity. The drape comprises a duct 905 situated within the cavity and attached to the drape in a helical arrangement. Although in a helical arrangement, the duct still extends along the longitudinal extent of the cavity of the drape in the sense that the terminal openings of the duct 907 and 909 span a distance in the longitudinal direction of the cavity. This helical arrangement may be particularly effective at providing cooling to a robotic arm when used in combination with the feature of having one or more ports situated between the terminal end points, as illustrated in FIG. 8. This is because a duct in a helical arrangement with one or more ports would enable fluid to be channelled to and from multiple sides of the robotic arm, thereby providing more flexibility in determining where on the arm to channel fluid to and from.

Thus far embodiments have been described in which a surgical robotic arm drape comprises a duct for channelling fluid to and from a portion of a robotic arm housed within the cavity defined by the exterior sheet of the drape. In alternative embodiments, the robotic arm may comprise surface features extending along the longitudinal extent thereof that are configured to cooperate with a surgical robotic arm drape enveloping a portion of the robotic arm to define a duct for channelling fluid to and from the robotic arm.

Figure 10:
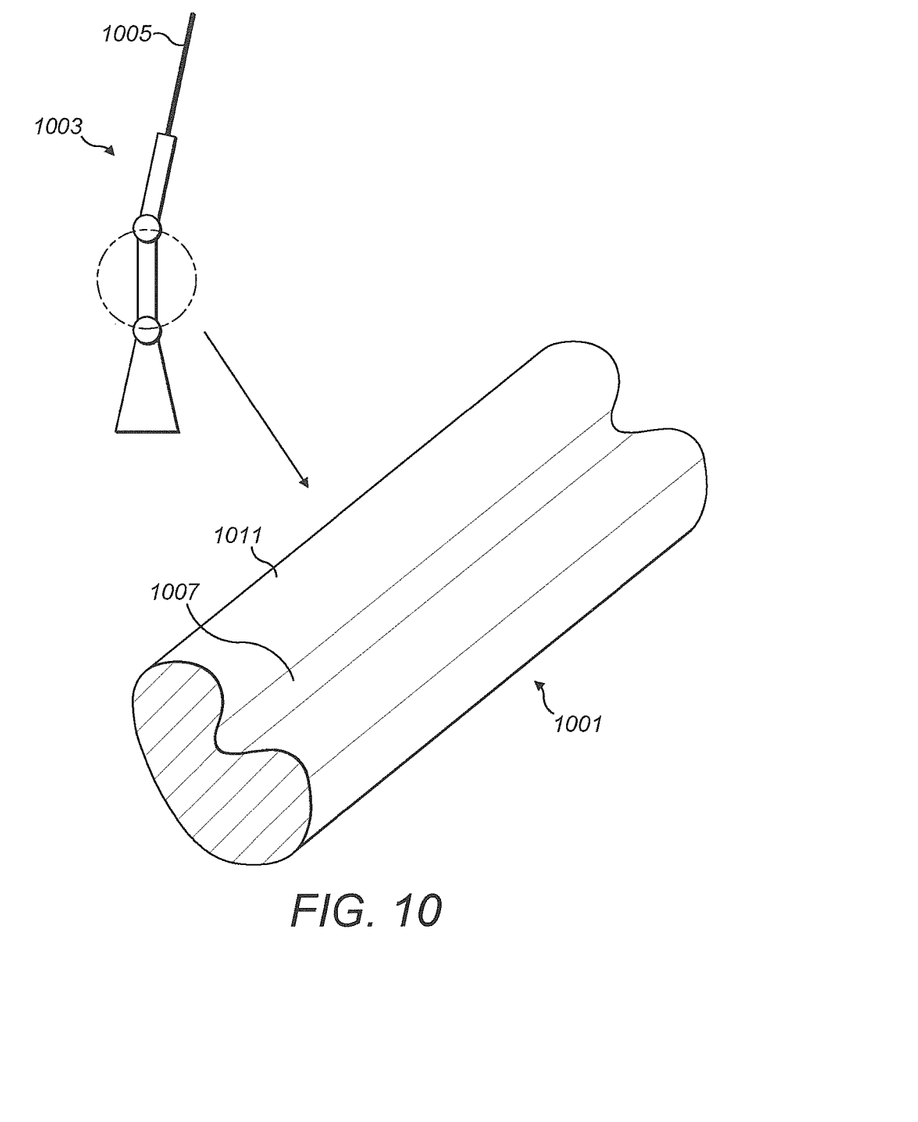
FIG. 10 shows a robotic arm comprising surface features.

FIG. 10 shows a section 1001 of a robotic arm 1003. The robotic arm is attached at one of its ends to a surgical instrument for performing surgery, as previously described.

The robotic arm comprises a surface feature in the form of a channel, or groove 1007 that extends along the longitudinal extent of the robotic arm. Although only a segment of the robotic arm is shown as comprising the channel/groove, it will be appreciated that the groove may extend along the entire length of the arm to be housed within the cavity of a surgical drape, or along a substantial portion of the arm. In alternative embodiments the robotic arm may comprise two or more grooves or channels.

When the robotic arm is housed within the cavity defined by an exterior sheet of a surgical drape, the channel 1007 cooperates with the drape to define a duct 1009 for channelling fluid to or from the robotic arm. When the drape is placed over the exterior surface 1011 of the arm, the duct would be bounded on one side by the surface of the channel and on the other side by the drape.

The robotic arm may further comprise an internal duct (not shown) for channelling cooling fluid along the arm as previously described. In this manner the internal duct and the duct defined by the channel and drape together provide a fluid path for fluid to flow both to and from a robotic arm housed in a drape.

If fluid were to be driven or blown through duct 1009 from an external source (e.g. a fan), the pressure in the region between the channel 1007 and drape may be higher than the pressure on the exterior side of the drape, causing the drape to be blown outwards from the exterior surface 1011 of the robotic arm, reducing the effectiveness of the duct. One way to overcome this problem would be to secure the drape to the outer surface of the robotic arm, for example using a tie or elastic band.

If fluid were to be drawn out through the duct 1009 away from the robotic arm, for example by placing the outlet of the duct near the opening of the cavity under suction, there may exist a negative pressure in the region between the channel 1007 and drape relative to the exterior of the drape. This may lead to the shrink-wrap effect discussed above. In order to prevent the drape from becoming flush with the surface of the channel 1007 and closing the fluid path, the robotic arm may comprise a mesh, or grill, or grating over the channel. The mesh could for example be attached to the outer surface of the robotic arm at positions adjacent to the channel. In the presence of a negative pressure in the duct, the drape would be drawn towards or sucked onto the mesh, and thus the mesh acts to maintain an open fluid path.

Figure 11:
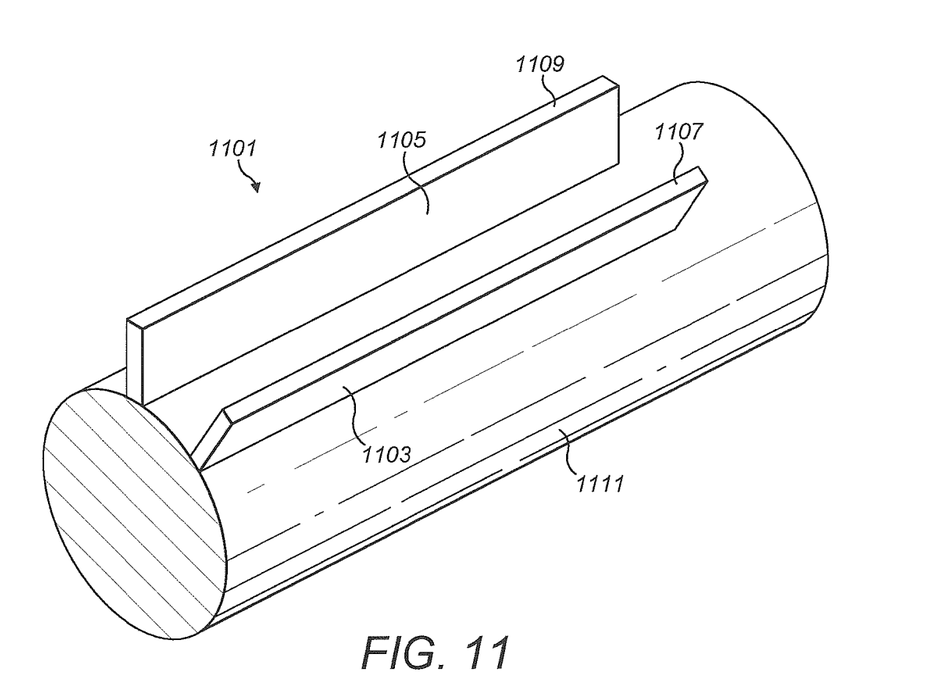
FIG. 11 shows a robotic arm comprising surface features.

In an alternative embodiment the robotic arm may comprise a plurality of ribs projecting substantially radially outward from the robotic arm, as illustrated in FIG. 11. FIG. 11 shows a segment of a robotic arm 1101 comprising a plurality of ribs 1103 and 1105 each projecting radially out from the arm. Although only two ribs are shown in FIG. 11, it will be appreciated that the arm may comprise any suitable number of ribs.

When the robotic arm is housed within a cavity defined by the drape, the drape cooperates with the ribs to define a duct for channelling fluid to and from the robotic arm. Suitably, the drape rests on the upper edges 1107 and 1109 of ribs 1103 and 1105 respectively so that the duct is bound by the ribs, the drape, and the outer surface 1111 of the arm. The robotic arm 1101 may further comprise a mesh or grill for preventing the drape from closing the fluid path through the duct when there exists a negative pressure in the duct relative to the exterior of the drape. The mesh may be configured to overlay the ribs, or alternatively it may be attached to the inner side surfaces of the ribs.

Configuring the robotic arm to comprise surface features that cooperate with the drape to define a duct may advantageously provide a cooling mechanism for the robotic arm that is compatible with a standard surgical robotic arm drape.

The combination of a surgical robotic arm and a surgical robotic arm drape form a surgical robotic apparatus for performing robotic surgery. The surgical robotic arm drape comprises an exterior sheet that defines an elongate cavity for housing a portion of the robotic arm. In accordance with the embodiments herein described, the surgical robotic apparatus comprises a longitudinal features that are operable to space the exterior sheet of the drape from an outer surface of the robotic arm when there is a negative pressure within the cavity relative to an adjacent region exterior of the cavity. The longitudinal features space the exterior sheet from the outer surface of the arm to define a fluid path to channel fluid to or from the robotic arm.

The longitudinal features may comprise the duct itself in accordance with the embodiments described with reference to FIGS. 3 and 4. The longitudinal features may comprise spacing elements positioned within the duct, for example the ribs or the plurality of projections previously described. The longitudinal features may comprise ribs that partly define the duct in accordance with the embodiments described with reference to FIG. 7.

Alternatively or in addition the longitudinal features may be the surface features of the robotic arm in accordance with the embodiments described with reference to FIGS. 10 and 11.

Thus, the drape can be adapted to envelope a surgical arm. The drape may be shaped to define an elongate cavity for surrounding substantially all of a surgical arm. The drape may be substantially closed at its distal end, apart optionally for a port to permit an instrument to extend through the drape. The drape may be open at its proximal end, permitting it to be passed over the arm and then, optionally, sealed against the arm to enclose a volume between the interior of the drape and the exterior of the arm.

In one example, the drape may include a single duct or passage that runs from at or near the mouth of the drape to a point near the distal end of the cavity. The duct may be attached to the interior or the exterior surface of the drape. The distal end of the duct is arranged to open on to the arm, or to connect with the arm for directing fluid from an opening of the duct near the mouth of the drape to the arm, or vice versa. The duct may have multiple openings along its length for permitting fluid to play on to the arm, or for drawing fluid from the vicinity of the arm. The drape may have two such ducts: one for passing fluid to the arm and one for passing fluid from the arm. The drape may have a plurality of such ducts for opening on to, or connecting with, multiple locations on the arm. Each of the plurality of ducts is arranged to direct fluid from an opening of the duct to the arm, or vice versa. Each duct may be fully or partially defined by material integral with the exterior sheet of the drape in accordance with any of the examples described herein. Thus, for example, the duct could be defined on three sides by the drape, and the remaining side could be defined by the exterior of the arm when the drape is in place on the arm. Each duct may be defined at least in part by the exterior surface of the arm: for example the exterior surface of the arm could define the duct on three sides and the remaining side could be defined by the drape when it is in place on the arm. Where the duct or passage is defined by the drape and the arm in cooperation it is preferred that in use a negative static pressure is maintained in that region so that the action of atmospheric pressure on the drape will tend to close the passage. If the drape has a plurality of ducts, each of the plurality of ducts need not be defined in the same way; the ducts may be defined in accordance with any combination of the examples described herein. The drape comprises a surgical barrier sheet for defining the cavity around the arm. The sheet may be flexible.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

The invention claimed is:

1. A surgical robotic arm drape for enveloping a portion of a robotic arm, the drape comprising:
an exterior sheet defining an elongate cavity for housing a portion of a robotic arm; and
a duct defined in part by material integral with the exterior sheet and in part by the exterior sheet, the duct defining a fluid path along the longitudinal extent of the cavity to channel fluid to or from a robotic arm housed within the cavity.

2. A surgical robotic arm drape as claimed in claim 1, wherein said material is in a nested arrangement with the exterior sheet along the longitudinal extent of the cavity.

3. A surgical robotic arm drape as claimed in claim 2, wherein said material is in a concentric arrangement with the exterior sheet along the longitudinal extent of the cavity.

4. A surgical robotic arm drape as claimed in claim 1, wherein the duct comprises a first opening configured so as to be positioned in the vicinity of a robotic arm housed within the cavity, and a second opening configured so as to be in the vicinity of an opening in the cavity, and wherein the drape comprises spacing elements positioned within the duct so as to maintain an open fluid path when there exists a negative pressure in the duct relative to the exterior of the drape during use caused by the second opening being under suction.

5. A surgical robotic arm drape as claimed in claim 4, wherein the spacing elements comprise a plurality of projections extending at least partly between the said material and the exterior sheet.

6. A surgical robotic arm drape as claimed in claim 1, wherein the duct is defined by a plurality of ribs integral with the exterior sheet.

7. A surgical robotic arm drape as claimed in claim 6, wherein the ribs are configured so as to connect to an exterior surface of a robotic arm housed within the cavity during use.

8. A surgical robotic arm drape as claimed in claim 1, wherein the duct comprises first and second terminal openings and at least one port situated between the first and second terminal openings, the at least one port arranged to channel fluid to and from a respective at least one location on a robotic arm housed within the cavity.

* * * * *